(12) United States Patent
Katagi

(10) Patent No.: US 6,829,954 B2
(45) Date of Patent: Dec. 14, 2004

(54) SAMPLE PRETREATMENT SYSTEM

(75) Inventor: Hitomi Katagi, Tokyo (JP)

(73) Assignee: Aloka Co., Ltd. (JP)

( * ) Notice: Subject to any disclaimer, the term of this patent is extended or adjusted under 35 U.S.C. 154(b) by 32 days.

(21) Appl. No.: 10/402,319

(22) Filed: Mar. 28, 2003

(65) Prior Publication Data

US 2003/0213313 A1 Nov. 20, 2003

(30) Foreign Application Priority Data

Mar. 29, 2002 (JP) ........................................ 2002-094293

(51) Int. Cl.[7] ............................................. G01N 35/10
(52) U.S. Cl. .................................................. 73/864.25
(58) Field of Search ........................ 73/864.01, 864.02, 73/864.24, 864.25, 864.81, 864.82, 864.83, 864.84, 864.85, 864.86, 864.87; 422/100, 101

(56) References Cited

U.S. PATENT DOCUMENTS

| | | | |
|---|---|---|---|
| 4,276,051 A | | 6/1981 | Ginsberg et al. |
| 4,276,258 A | | 6/1981 | Ginsberg et al. |
| 4,647,432 A | | 3/1987 | Wakatake |
| 4,805,469 A | * | 2/1989 | Commarmot ............ 73/864.81 |
| 6,355,164 B1 | * | 3/2002 | Wendell et al. .......... 210/198.2 |
| 6,599,476 B1 | * | 7/2003 | Watson et al. ................ 422/63 |
| 2001/0053335 A1 | * | 12/2001 | Hashimoto et al. ........... 422/65 |

FOREIGN PATENT DOCUMENTS

| | | | |
|---|---|---|---|
| DE | 4210963 | 10/1993 | .......... G01N/35/02 |
| EP | 0753747 | 1/1997 | .......... G01N/35/04 |
| JP | 10-024911 | 1/1998 | ............. B65C/3/02 |

\* cited by examiner

Primary Examiner—Charles Garber
(74) Attorney, Agent, or Firm—Marger Johnson & McCollom, P.C.

(57) ABSTRACT

A sample pretreatment system is provided with a pipettig table. On the pipetting table, there are provided on its front side a normal area 57 in which a plurality of normal secondary sample racks 56 are placed and on its back side an urgent area 76 in which a plurality of urgent secondary sample racks 77 are placed. Each of the normal secondary sample racks 56 holds a plurality of normal secondary sample containers 60 and each of the urgent secondary sample rack 77 holds a plurality of urgent secondary sample containers 79. In a normal pipetting mode, a sample is pipetted from a normal source sample container to the normal secondary sample containers 60, and in an urgent mode, a sample is pipetted from a source sample container to the urgent secondary sample containers 79. The urgent secondary sample rack 77 is formed into a portable type and has a size smaller than the normal secondary sample rack 56. According to this sample pretreatment system, secondary sample containers to which an urgent source sample has been pipetted can be located easily.

5 Claims, 3 Drawing Sheets

SAMPLE PRETREATMENT SYSTEM

BACKGROUND OF THE INVENTION

1. Field of the Invention

The present invention is related to a sample pretreatment system, and in particular to a sample pretreatment system provided with secondary sample racks.

2. Description of the Prior Art

In a sample pretreatment system which is equipped with an automatic pipetting apparatus for subdividing (pipetting) a source sample such as a blood sample or the like into a plurality of secondary sample containers, there is provided a secondary sample rack in which a plurality of secondary sample containers are held in rows. When pipetting a source sample, a pipetting nozzle is moved to a source sample container containing a source sample to be pipetted and then aspirates the source sample for a predetermined amount. Thereafter, the pipetting nozzle is moved to a secondary sample rack with keeping the aspirated source sample therein, and then dispenses a predetermined amount of the sample to secondary sample containers. When the pipetting operation is completed for all the predetermined secondary sample containers, the secondary sample rack is taken out and fed to the next stage for examination or analysis or the like.

However, in the conventional system described above, when a source sample has to be pipetted urgently, there arises a problem upon taking out and feeding the secondary sample rack to the next stage. Specifically, when an urgent source sample has to be pipetted during normal pipetting operations, an urgent source sample rack is placed in the system manually, and pipetting of the sample is carried out preferentially. However, in this preferential pipetting operation, the sample is pipetted to secondary sample containers held in the secondary sample rack in the same manner as the normal pipetting operation. The secondary sample rack is taken out after the pipetting of the sample for all the secondary sample containers held in the rack have been completed as described above. Therefore, even though the pipetting operation of the urgent source sample is preferentially carried out, it is not possible to feed the secondary sample rack to the next stage for examination until the pipetting of the sample for all the predetermined secondary sample containers has been completed, thus loss of time can not be avoided.

In order to avoid such loss of time, in a practical site only secondary sample containers to which the urgent sample has been pipetted are selected from the secondary sample rack to pick up them manually. However, this needs to locate the secondary sample containers to which the urgent source sample has been pipetted from among all the secondary sample containers held in the secondary sample rack, and thus this operation is quite troublesome for a user. As described above, in the conventional system, it is troublesome to feed the secondary sample containers containing the urgent source sample into the next stage.

SUMMARY OF THE INVENTION

In view of the above problem in the conventional system, it is an object of the present invention to provide a sample pretreatment system which does not necessitate to locate secondary sample containers to which an urgent source sample has been pipetted.

It is another object of the present invention to provide a sample pretreatment system capable of feeding secondary sample containers to which an urgent source sample has been pipetted into the next stage immediately.

In order to achieve the above objects, the present invention is directed to a sample pretreatment system. The sample pretreatment system comprises: a pipetting nozzle for pipetting a sample from a source sample container to secondary sample containers; a nozzle conveying apparatus for conveying the pipetting nozzle; a normal area in which at least one normal secondary sample rack which holds a plurality of normal secondary sample containers is placed; an urgent area in which at least one urgent secondary sample rack which holds a plurality of urgent secondary sample containers is placed; and control means for controlling the pipetting nozzle and the nozzle conveying apparatus, the control means controls the pipetting nozzle and the nozzle conveying apparatus so that in a normal pipetting mode a sample from the source sample container is pipetted to the secondary sample containers, and in an urgent pipetting mode a sample from the source sample container is pipetted to the urgent secondary sample containers.

According to the above structure, in the normal pipetting mode, a source sample is pipetted to normal secondary sample containers in the normal area as is the same with the conventional system, and in the urgent pipetting mode, a source sample is pipetted to urgent secondary sample containers in the urgent area which is separately arranged from the normal area. Therefore, since the urgent secondary sample containers are positioned in the urgent area, it is possible to locate them easily without looking for and selecting them as was done in the conventional system. As a result, it is possible to feed such urgent secondary sample containers to the next stage immediately. In this connection, the urgent secondary sample rack may be formed into a portable type or it may be fixedly mounted to a pipetting table.

Preferably, the sample pretreatment system may further include a pipetting table on which the normal area and the urgent area are provided, the pipetting table having a front side and the a back side, in which the normal area is arranged on the front side of the pipetting table and the urgent area is arranged on the back side of the pipetting table. Here, the front side of the pipetting table means the side of the table where an operator stands, and the back side means the opposite side of the front side. Normally, the pipetting table has a relatively large free space at the back side thereof. Therefore, according to this arrangement, it is possible to provide the urgent area on the back side of the pipetting table by utilizing such a relatively large free space effectively with the normal area for the normal secondary sample racks which are frequently replaced with other one being provided on the front side of the pipetting table. Further, without enlarging the width of the pipetting table, it is possible to provide such urgent area.

Further, preferably, the urgent secondary sample rack is formed into a portable type, and has a size smaller than the normal secondary sample container. Since the urgent secondary sample rack is not so frequently used, it is not required to have a large size. Further, it is better for the urgent secondary sample rack to be formed into a portable type having a small size because handlability is good and feeding to the next stage can be made easily.

Another aspect of the present invention is also directed to a sample pretretment system. This sample pretretment system comprises: a pipetting nozzle for pipetting a sample from a source sample container to secondary sample containers: a nozzle conveying apparatus for conveying the pipetting nozzle: a normal area in which at least one normal secondary sample rack which holds a plurality of secondary sample containers is placed; an urgent area in which at least one urgent secondary sample rack which holds a plurality of urgent secondary sample containers is placed; a container transferring apparatus for carrying out container transfer by which a unused normal secondary sample container in the normal secondary sample rack is transferred to the urgent secondary sample rack as an urgent secondary sample container, and control means for controlling the pipetting nozzle, the nozzle conveying apparatus and the container transferring apparatus so that in a normal pipetting mode a sample from the source sample container is pipetted to the secondary sample containers, and in an urgent pipetting mode the container transfer is carried out, and after the container is transferred, s sample from the source sample container is pipetted to an urgent secondary sample container which has been transferred from the normal secondary sample rack.

According to this structure, when a sample is required to be pipetted urgently, it is not necessary to prepare urgent secondary sample containers in advance separately from the normal secondary sample containers, and unused normal secondary sample containers held in the normal secondary sample rack can be used as urgent secondary sample containers.

In this case, preferably, the label sticking is carried out during the transfer of the container. According to this, it is no longer necessary to stick a label after the transfer of the container is completed, thereby enabling to simplify the steps for preparation for the urgent secondary sample containers.

The above and other objects, structures and advantages of the present invention will be more apparent when the following detailed description of the embodiment is considered in conjunction with the appended drawings.

DETAILED DESCRIPTION OF THE PREFERRED EMBODIMENTS

The preferred embodiments of the present invention will now be described in detail with reference to the drawings.

Figure 1:
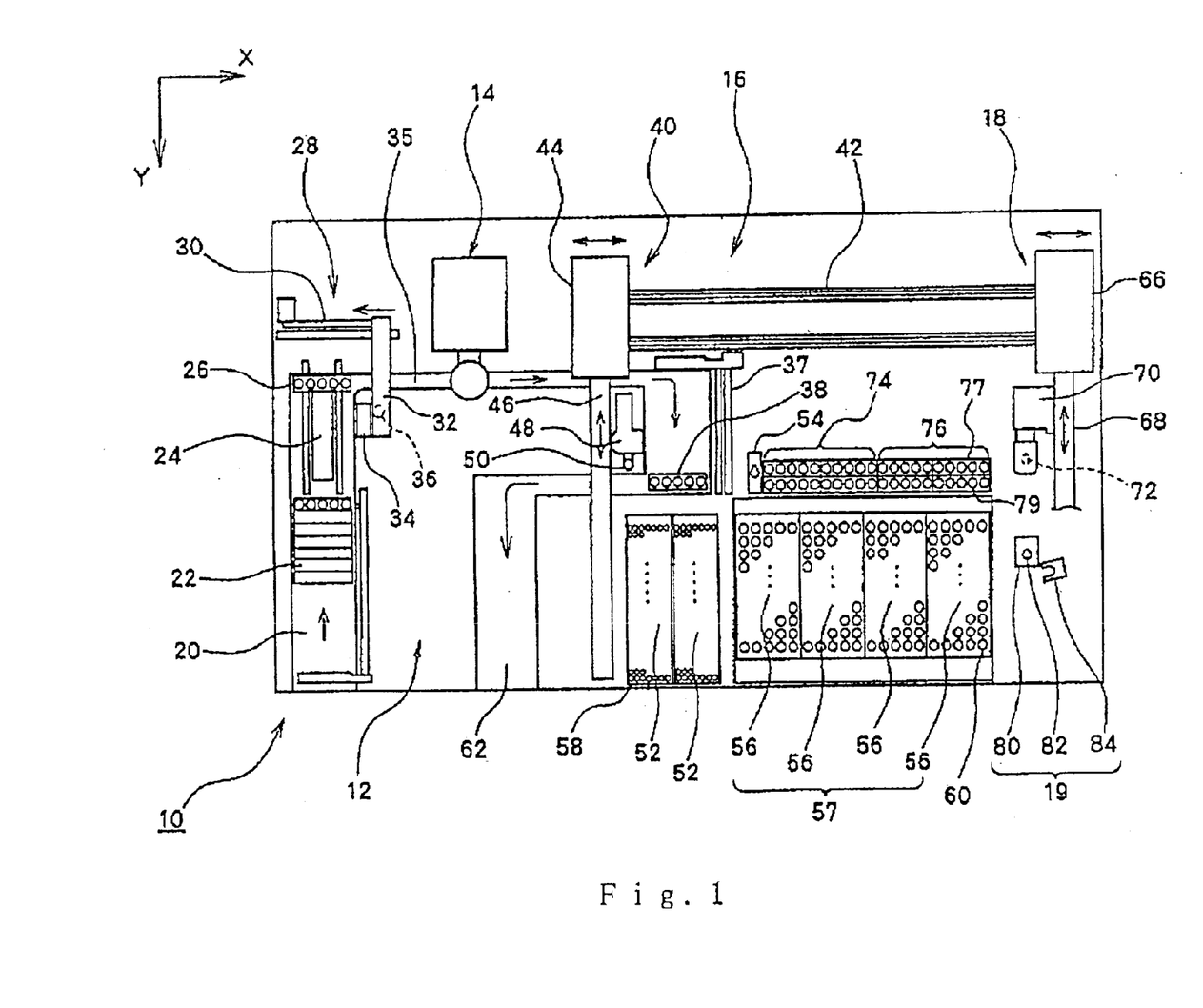
FIG. 1 is a top view which shows the overall structure of one embodiment of a sample pretreatment system according to the present invention.

FIG. 1 is a top view which shows the overall structure of a sample pretreatment system 10. The sample pretreatment system 10 is equipped with a source sample rack conveying apparatus 12 which sequentially conveys source sample racks in which source sample containers are arranged to a pipetting position, a cap opening unit 14 which removes the cap of a source sample container for enabling pipetting operation to be carried out, a pipetting apparatus 16 which uses a nozzle and a pipetting pump to subdivide (pipette) the source sample in the source sample container to a plurality of secondary sample containers arranged in a secondary sample rack, a container conveying apparatus 18 which conveys containers, and a label sticking apparatus 19 which sticks labels on containers. The control of all the operations of the sample pretreatment system 10 is carried out by a control section not shown in the drawings, and all the operations of the sample pretreatment system 10 are displayed on a display not shown in the drawings. The X-axis direction and the Y-axis direction are shown in FIG. 1 to make it easy to understand the conveying direction of the source sample rack and the like. The Z-axis direction is orthogonal to the plane of the paper.

Source sample racks 22 are placed in a rack receiving portion 20 of the source sample rack conveying apparatus 12 by a manual operation or by the use of a separate apparatus. The source sample racks 22 are placed in the rack receiving portion 20 so that the longitudinal direction of each rack is directed to the X-axis direction. The placed source sample racks 22 are fed forward along a feeding path in the Y-axis direction by a feeding mechanism. A rack separation mechanism 24 provided at a predetermined separation position separates the head source sample rack 22 from the placed source sample racks 22. The separated source sample rack 22 is moved by the moving mechanism in the Y-axis direction to a label reading position 26, and is set at such position.

The source sample rack conveying apparatus 12 has a detection unit conveying mechanism 28 which includes a moving arm 32 which can move along a first guide rail 30 in the X-axis direction. The moving arm 32 extends over the top of the source sample rack 22 set at the label reading position 26, and a label reader 34 and a container presence/absence detection sensor 36 are arranged so as to hang downward at the tip portion thereof. The label reader 34 and the container presence/absence detection sensor 36 are arranged to face the side surface of the source sample rack 22 which is opposite to the side surface of the source sample rack 22 facing to the first guide rail 30. A bar code reader can be used for the label reader 34, for example, and a reflection-type optical sensor can be used for the container presence/absence sensor 36, for example.

In the structure described above, by controlling the detection unit conveying mechanism 28, the moving arm 32 can be moved in the X-axis direction so that the label reader 34 and the container presence/absence sensor 36 can be moved in the X-axis direction, namely, in the direction along which the containers are arranged in the source sample rack. In this way, the detection of the presence or absence of each container is sequentially carried out by the container presence/absence sensor 36, and the bar code of the label stuck on each container is also sequentially read out by the label reader 34. The read out data is transmitted to a control section not shown in the drawings.

The source sample rack 22 having the containers of which labels have been read out by the label reader 34 is then conveyed to the position of the cap opening unit 14 by a belt line 35 which moves in the X-axis direction. The cap opening unit 14 carries out a cap opening operation on each container. Namely, because a container such as a blood sample vial is provided with a rubber cap or the like to prevent contamination, the cap is removed by the cap opening unit 14 before pipetting operation.

The source sample rack 22 that has undergone the cap opening operation is conveyed further along the X-axis direction by the belt line 35, and then this source sample rack 22 is moved in the Y-axis direction and set at a pipetting position 38 by a setting mechanism 37.

As described above, by the cooperation of the source sample rack conveying apparatus 12 and the cap opening unit 14, the source sample rack placed in the rack receiving portion 20 is fed to the label reading position at which labels attached to the source sample containers are read out, then fed to the cap opening unit 14 at which the caps of the containers are removed, and then set at the pipetting position 38 for pipetting operation.

The above described processes are the common for a normal pipetting mode in which a normal pipetting operation is carried out and an urgent pipetting mode in which pipetting operation for an urgent source sample is carried out. In this regard, however, please note that in the urgent pipetting mode, a source sample contain is recognized as an urgent source sample container by reading a label attached thereto, and based on the readout information a control section not shown in the drawings carries out a different control for the subsequent pipetting operation.

Next, a description will be made with regard to the pipetting apparatus 16. The pipetting apparatus 16 includes a nozzle conveying mechanism 40 which can convey the nozzle freely in the three axial directions of the X-axis, the Y-axis and the Z-axis. The nozzle conveying mechanism 40 is equipped with two second guide rails 42 arranged in the X-axis direction, a first base 44 which can move in the X-axis direction on the second guide rails 42, a first Y-axis arm 46 which is integrally formed with the first base 44 to extend in the Y-axis direction, and a nozzle pedestal 48 which can move in the X-axis direction along the first Y-axis arm 46, wherein a pipetting nozzle 50 is provided on the nozzle pedestal 48. The pipetting nozzle 50 is movable in the Z-axis direction with respect to the nozzle pedestal 48. The pipetting nozzle 50 is constructed from a nozzle base and a nozzle tip which is removably attached to the nozzle base. Further, the nozzle pedestal 48 is also provided with a pipetting pump connected to the pipetting nozzle 50 with a piping tube or the like. Of course, the pipetting pump may be separately arranged outside the nozzle pedestal 48.

Further, the above-described pipetting position 38 is established inside the space in which the pipetting nozzle 50 can be conveyed by the nozzle conveying mechanism 40 Inside this space, there are provided a plurality of tip racks 52, a tip remover 54, a normal area 57 in which normal secondary sample racks 56 are to be placed and an urgent area 76 in which urgent secondary sample racks 77 are to be placed.

Each of the tip racks 52 holds a plurality of rows of unused nozzle tips 58. These tips are arranged so that the tip head openings in which the nozzle base is inserted are facing upward.

Namely, the unused nozzle tips 58 are arranged with their tip head openings facing upward to enable the unused nozzle tips 58 to fit onto the nozzle base when the nozzle base is lowered in the Z-axis direction. It is possible to provide a plurality of tip racks 52 according to the treatment capacity of the system.

The tip remover 54 hooks onto each of the used nozzle tips to remove it from the nozzle base. A tip disposal container not shown in the drawings is arranged directly below the tip remover 54, and the removed used nozzle tips are disposed of by being dropped into the tip disposal container.

The normal area 57 is an area in which normal secondary sample racks used in the normal pipetting mode are placed, and this area is provided on the front side of a pipetting table. Here, please note that the pipetting table means a working table on which the normal secondary sample racks 56, the tip racks 52, the urgent secondary sample racks 77 and the like are placed, and the front side of the pipetting table means the side of the table where an operator stands. In the normal area 57, at least one normal secondary sample rack 56 which holds a plurality of normal secondary sample containers 60 is placed. In the example shown in FIG. 1, four normal secondary sample racks 56 are placed. When the system begins operation or when the normal secondary sample racks are to be replaced, an operator sets a plurality of normal secondary sample racks 56 holding only unused secondary sample containers in the normal area from the front side of the pipetting table.

The urgent area 76 is an area in which urgent secondary sample racks 77 are placed, and this area is provided on the back side of the pipetting table. In this urgent area 76, at least one urgent secondary sample rack 77 is placed. Each urgent secondary sample rack 77 holes a plurality of urgent secondary sample containers 79. In the example shown in FIG. 1, four urgent secondary sample racks 77 each holding five urgent secondary sample containers 79 are placed in the urgent area 76. Each urgent secondary sample rack 77 is formed into a portable type and has a size smaller than the normal secondary sample rack 56.

The pipetting sequence is carried out as follows under the control of a control section not shown in the drawings. First, operations start in a state in which a nozzle tip is not attached to the nozzle base. Accordingly, the nozzle conveying mechanism 40 is operated- to move the nozzle base in a horizontal direction to a position directly above the tip rack 52. Then, the nozzle base is lowered toward the tip head opening of one unused nozzle tip 58 selected from the group of unused nozzle tips 58 until the nozzle base is pushed into the tip head opening of such selected unused nozzle tip 58, whereby the pipetting nozzle 50 is formed. Next, the pipetting nozzle 50 is raised to a prescribed height, and then the pipetting nozzle 50 is moved in a horizontal direction to a position directly above a source sample container containing a source sample to be pipetted at the pipetting position 38. In this way, preparation for the pipetting operation is setup.

Next, the pipetting nozzle 50 is lowered, and then a predetermined amount of the source sample is aspirated inside the nozzle tip by operating and controlling the pipetting pump. For example, when subdividing a source sample to three secondary sample containers, the predetermined amount would be the total amount necessary for creating three secondary samples.

Next, with the predetermined amount of source sample being held inside the nozzle tip, the pipetting nozzle 50 is raised to a predetermined height, and then the pipetting nozzle 50 is moved so that it is positioned directly above a secondary sample container 60 to which the source sample is to be pipetted. In this regard, it is to be noted that in the normal pipetting mode, a secondary sample container to which the source sample is to be pipetted is a normal secondary sample container held in the normal secondary sample rack 56, and in the urgent pipetting mode, a secondary sample container to which the sample is to be pipetted is an urgent secondary sample container 79 held in the urgent secondary sample rack 77 placed in the urgent area 76. A control section now shown in the drawings designates these containers to which the source sample is to be pipetted. Then, the pipetting nozzle 50 is lowered at this position, and a predetermined amount of the source sample held inside the pipetting nozzle is dispensed by operating and controlling the pipetting pump. This sequence is then repeated to subdivide the source sample from one source sample container to a predetermined number of unused secondary sample containers.

When the pipetting operations for the source sample in one source sample container are completed, the pipetting nozzle 50 is moved in a horizontal direction so that the pipetting nozzle 50 is positioned directly above the tip remover 54. Then, the nozzle 50 is lowered, and after the used nozzle tip is hooked by the tip remover 54, the pipetting nozzle 50 is raised to a predetermined height, whereby the used tip is removed from the nozzle base and falls into the tip disposal container arranged directly below the tip remover 54. Next, a new unused nozzle tip is attached to the nozzle base as described above, and the same sequence for pipetting a source sample from the next source sample container is carried out repeatedly.

When predetermined pipetting operations have been carried out from all the source sample containers arranged in one source sample rack, such source sample rack is conveyed along a conveying path and sent to a discharge section 62, and then the source sample rack is carried to the outside automatically or manually.

Next, a description will be given for the container conveying apparatus 18. The container conveying apparatus 18 is a mechanism which freely conveys a container held by a manipulator in the three axial directions of the X-axis, the Y-axis and the Z-axis. The container conveying apparatus 18 is equipped with the two second guide rails 42 arranged in the X-axis direction which are also utilized by the nozzle conveying mechanism 40, a second base 66 which can move in the X-axis direction on the second guide rails 42, a second Y-axis arm 68 which is integrally formed with the second base 66 to extend in the Y-axis direction, and a manipulator pedestal 70 which can move in the X-axis direction along the second Y-axis arm 68, wherein a manipulator 72 is provided on the manipulator pedestal 70. The manipulator 72 is movable. In the Z-axis direction with respect to the manipulator pedestal 70.

Because the second guide rails 42 are utilized by both the container conveying apparatus 18 and the nozzle conveying mechanism 40, the area where the manipulator 72 can be moved covers a wide area up to the source sample rack at the pipetting position. Therefore, by using the manipulator 72, it is possible to convey containers to an abnormal source sample elimination area 74, the urgent are 76 and the label sticking apparatus 19 which are provided inside the area of such movement, respectively.

The abnormal source sample elimination area 74 is an area for receiving a source sample container containing a sample recognized as an abnormal source sample. The cases where a source sample is recognized as an abnormal source sample can include cap opening mistakes, pipetting mistakes and the like in addition to the case where there are label reading errors or errors in the recognition of the presence or absence of a container at the label reading position 26, for example. The source sample container recognized as containing such an abnormal source sample is temporarily sent to the pipetting position 38. Then, by operating the container conveying apparatus 18 in accordance with Instructions from a control section not shown in the drawings, the manipulator 72 is moved directly above the abnormal source sample container at the pipetting position 38, and after being lowered to grasp the abnormal source sample container, the manipulator 72 is raised to a predetermined height and then moved directly above the abnormal source sample elimination area 74. Then, the manipulator 72 is lowered at the position of a predetermined container holding location inside the abnormal source sample elimination area 74, and the grip is released to store the abnormal source sample container at such a location.

Further, in the urgent area 76, the urgent secondary sample rack 77 is placed, as described above. Before receiving the secondary sample containers, there is no container in this area 76. Therefore, the manipulator 72 grasps an unused normal secondary sample container from the normal secondary sample rack 56, and conveys it to the label sticking apparatus 19 as an urgent secondary sample container 79 according to control by a control section not shown in the drawings. After the label sticking apparatus 19 sticks a predetermined label on the urgent secondary sample container 79, the manipulator 72 conveys the urgent secondary sample container 79 to which the label has been stuck from the label sticking apparatus 19 to the urgent secondary sample rack 77. In this way, it is possible to transfer an unused normal secondary sample container from the normal secondary sample rack 56 to the urgent secondary sample rack 77 as an urgent secondary sample container 79.

Alternatively, it is also possible to pipet a sample in an urgent source sample container to secondary sample containers in the normal secondary sample rack 56, and after the pipetting of the sample has been carried out, the secondary sample container to which the sample has been pipetted is transferred from the normal secondary sample rack 56 to the urgent secondary sample rack 77 as an urgent secondary sample container 79 using the manipulator 72.

Next, a description will be made with regard to the label sticking apparatus 19. The label sticking apparatus 19 is equipped with a label sticking device 80 and a container holding device 82, and cooperates with a transfer mechanism 84 for conveying secondary sample containers. The label sticking device 80 prepares predetermined labels which will be stack to secondary sample containers, and sticks a label to a secondary sample container received by the container holding device 82. In the label sticking process, data of the source sample container obtained at the label reading position 26 are transmitted so that this process can be carried out in parallel with the pipetting operation.

By repeatedly carrying out the series of the processes described above, it is possible to carry out pipetting of a source sample and label sticking efficiently.

Hereinbelow, a detailed description will be made with regard to the urgent pipetting mode. When it is necessary to pipet a sample from a source sample container urgently, a user inputs pipetting information which indicates that an urgent pipetting should be carried out into the system. In addition to this, an urgent source sample rack which holds an urgent source sample container containing an urgent source sample is placed in the rack receiving portion 20. The urgent source sample is fed along the conveying path to be set at the label reading position 26 according to the operation of the source sample rack conveying apparatus 12. At the label reading position 26, a label attached to the urgent source sample container is read by the label reader 34, and the read out data is transmitted to the control section not shown in the drawings, and then the data is compared with the pipetting information inputted by the user to be recognized as the source sample container being an urgent source sample container. At that time, the control mode of this system for this urgent source sample container is changed into the urgent pipetting mode, and therefore conveyance of the urgent source sample and preparation of urgent secondary sample containers are carried out in a parallel operation.

Figure 2:
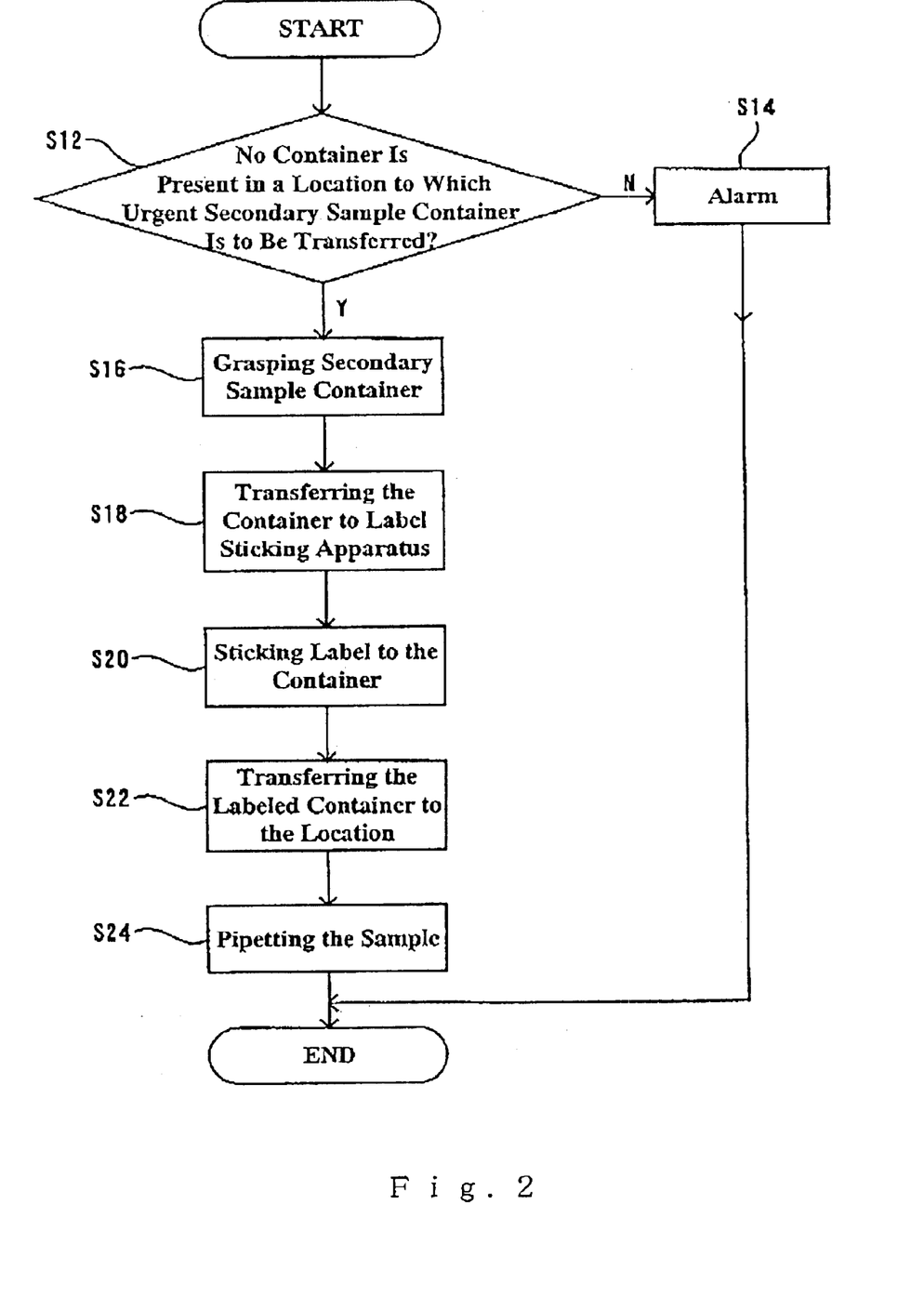
FIG. 2 is a flow chart which shows the process of preparing urgent secondary sample containers and carrying out pipetting operation in the embodiment of the sample pretreatment system of the present invention.
Figure 3:
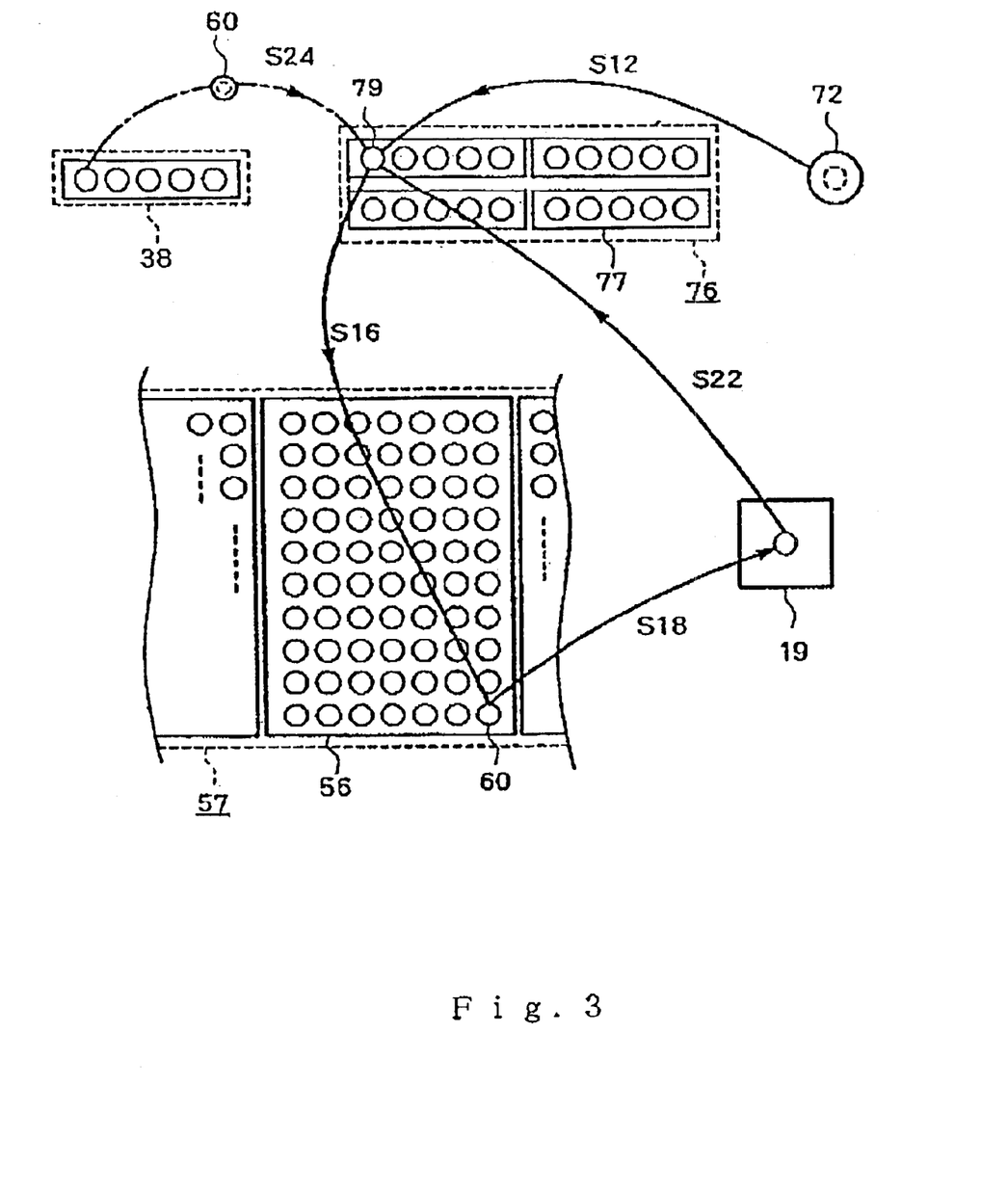
FIG. 3 is an illustration which shows the movements of a manipulator and a pipetting nozzle in an urgent pipetting mode in the embodiment of the sample pretreatment system of the present invention.

Next, based on the flow chart shown in FIG. 2, an explanation will be made with regard to the procedures for the preparation of the urgent secondary sample containers and the pipetting operation in the urgent mode. In this regard, it is to be noted that FIG. 3 shows the operations of the manipulator 72 and the pipetting nozzle 50 according to the procedures shown in FIG. 2. In FIG. 3, the motions of the manipulator 72 are shown by solid lines and the motions of the pipetting nozzle 50 are shown by dotted lines, and the corresponding steps in the procedures are indicated by the step number such as S12 and the like.

When the urgent pipetting is to be carried out, no secondary sample containers to which a sample is to be pipetted are prepared in the urgent area 76. Therefore, it is necessary to transfer urgent secondary sample containers to the urgent secondary sample rack 77. Therefore, at the first step, confirmation is made by the manipulator 72 as to whether or not there are any holes for supporting urgent secondary sample containers in the urgent secondary sample rack 77 (that is, there are any locations to which the urgent secondary sample containers are to be transferred), or as to whether or not other urgent secondary sample containers have already held therein (Step S12). In more details, in this step, the manipulator 72 is moved above the position where the secondary sample container is to be transferred, and at that position the manipulator 72 performs a gripping operation to confirm presence or absence of other urgent secondary sample container. When such other urgent secondary sample container is already existed, it is detected by a gripping force sensor of the manipulator 72. At that time, alarm is given (Step S14), and then the user removes the already existed urgent secondary sample container.

Where it is confirmed that there are no container at the location to which the urgent secondary sample container is to be transferred, the manipulator 72 is moved to a position above an unused normal secondary sample container in the normal secondary sample rack 56 according to the pipetting information to grasp the secondary sample container as an urgent secondary sample container 79 (Step S16). In this regard, the control section not shown in the drawings may instruct which unused normal secondary sample container is used as an urgent secondary sample container each time upon receiving the pipetting information, or it is also possible to determine such a container in advance. For example, it is possible to determine that unused normal secondary sample containers arranged in the last row of the normal secondary sample rack 77 are used as urgent secondary sample containers one by one from the last container in the row.

Next, the manipulator 72 transfers the urgent secondary sample container 79 to the label sticking apparatus 19 (Step S18) The label sticking apparatus 19 sticks a predetermined label to the container according to the pipetting information. After sticking the label, the manipulator 72 holds the labeled urgent secondary sample container 79 again to transfer it to a designation hole in the urgent secondary sample rack 77 (Step S22). When a plurality of urgent secondary sample containers are used, the steps from S16 to S22 are repeated for times corresponding to the number of the urgent secondary sample containers.

During the above operations, an urgent source sample container is fed along the belt line 35 to the cap opening unit 14, and after the cap is removed by the cap opening unit 14, the urgent source sample container is fed to the pipetting position 38. Namely, the conveyance of the source sample container and the preparation of the urgent secondary sample containers are carried out in parallel. This realizes an effective urgent pipetting operation. When the urgent source sample is set at the pipetting position 38 and the labeled urgent secondary sample container 79 is held by the urgent secondary sample rack 77, a source sample is aspirated from the urgent source sample container by the pipetting nozzle 50, and then the sample it dispensed to the urgent secondary sample container 79 to carry out pipetting operation (Step S24). When the pipetting operation has been carried out for all the urgent secondary sample containers 79, the urgent source sample container is fed to the discharge section 62 and then carried to the outside.

When the urgent pipetting is completed in this way, an alarm is given. Then, the user takes out the urgent secondary sample container 79 or the urgent secondary sample rack 77 in the urgent area 76. Since the urgent area 76 is provided separately from the normal area 57, it is possible to easily locate and take out the urgent secondary sample containers 79 without looking for and selecting them. Further, since the urgent secondary sample rack 77 is formed into a portable type and has a smaller size than the normal secondary sample rack, handling thereof is easy.

In the foregoing, a description is made with regard to the case where no urgent secondary sample containers are prepared in the urgent area, the present invention can be applied to the case where urgent secondary sample containers are in advance placed in the urgent secondary sample rack.

According to the sample pretreatment system of the present invention, since it is not necessary to look for and select the secondary sample containers to which an urgent source sample has been pipetted, the burden of the user can be reduced. Further, according to the sample pretreatment system of the present invention, it is also possible to send the secondary sample containers to which an urgent source sample has been pipetted to the next stage immediately.

Finally, it is needless to mention that the present invention is not limited to the above-described embodiments but can be modified or improved in various ways within the scope described in claims.

What is claimed is:

1. A sample pretreatment system, comprising:
   a pipetting nozzle for pipetting a sample from a source sample container to secondary sample containers;
   a nozzle conveying apparatus for conveying the pipetting nozzle;
   a normal area in which at least one normal secondary sample rack which holds a plurality of normal secondary sample containers is placed;
   an urgent area in which at least one urgent secondary sample rack which holds a plurality of urgent secondary sample containers is placed; and
   control means for controlling the pipetting nozzle and the nozzle conveying apparatus, the control means controls the pipetting nozzle and the nozzle conveying apparatus so that in a normal pipetting mode a sample from the source sample container is pipetted to the secondary sample containers, and in an urgent pipetting mode a sample from the source sample container is pipetted to the urgent secondary sample containers.

2. The sample pretreatment system as claimed in claim 1, further comprising a pippeting table on which the normal area and the urgent area are provided, the pipetting table having a front side and a back side, in which the normal area is provided on the front side of the pipetting table and the urgent area is provided on the back side of the pipetting table.

3. The sample pretreatment system as claimed in claim 1, wherein the urgent secondary sample rack is formed into a portable type, and has a size smaller than the normal secondary sample container.

4. A sample pretreatment system, comprising:

a pipetting nozzle for pipetting a sample from a source sample container to secondary sample containers;

a nozzle conveying apparatus for conveying the pipetting nozzle;

a normal area in which at least one normal secondary sample rack which holds a plurality of secondary sample containers is placed;

an urgent area in which at least one urgent secondary sample rack which holds a plurality of urgent secondary sample containers is placed;

a container transferring apparatus for carrying out container transfer by which a unused normal secondary sample container in the normal secondary sample rack is transferred to the urgent secondary sample rack as an urgent secondary sample container; and control means for controlling the pipetting nozzle, the nozzle conveying apparatus and the container transferring apparatus so that in a normal pipetting mode a sample from the source sample container is pipetted to the secondary sample containers, and in an urgent pipetting mode the container transfer is carried out, and after the container is transferred, s sample from the source sample container is pipetted to an urgent secondary sample container which has been transferred from the normal secondary sample rack.

5. The sample pretreatment system as claimed in claim 4, further comprising means for stacking a label onto the container during the transfer of the container.

* * * * *

UNITED STATES PATENT AND TRADEMARK OFFICE
CERTIFICATE OF CORRECTION

PATENT NO.     : 6,829,954 B2                                Page 1 of 1
DATED          : December 14, 2004
INVENTOR(S)    : Katagi It is certified that error appears in the above-identified patent and that said Letters Patent is hereby corrected as shown below:

Column 3,
Line 10, replace "container, and" with -- container: and --.

Column 6,
Line 29, replace "is operated- to" with -- is operated to --.

Column 7,
Line 37, replace "movable. In" with -- movable in --.
Line 59, replace "with Instructions" with -- with instructions --.

Column 8,
Line 35, replace "will be stack" with -- will be stuck --.

Column 9,
Line 50, replace "S18) The label" with -- S18). The label --.

Signed and Sealed this

Thirteenth Day of June, 2006

JON W. DUDAS
*Director of the United States Patent and Trademark Office*